(12) United States Patent
Pfrang et al.

(10) Patent No.: US 9,913,951 B2
(45) Date of Patent: Mar. 13, 2018

(54) DEVICE FOR OPENING CAPSULES

(71) Applicant: Gerresheimer Regensburg GmbH, Regensburg (DE)

(72) Inventors: Juergen Pfrang, Kallmuenz (DE); Vaclav Vojan, Plzen (CZ); Udo Leuschner, Regensburg (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 0 days.

(21) Appl. No.: 15/187,662

(22) Filed: Jun. 20, 2016

(65) Prior Publication Data

US 2016/0367768 A1    Dec. 22, 2016

(30) Foreign Application Priority Data

Jun. 22, 2015   (DE) .......................... 10 2015 109 996

(51) Int. Cl.
*A61M 15/00* (2006.01)
*B65B 69/00* (2006.01)

(52) U.S. Cl.
CPC ...... *A61M 15/0035* (2014.02); *A61M 15/003* (2014.02); *A61M 15/0041* (2014.02); *B65B 69/00* (2013.01); *A61M 2202/064* (2013.01)

(58) Field of Classification Search
CPC ........... A61M 15/0028; A61M 15/003; A61M 15/0033; A61M 15/0035; A61M 15/0036; A61M 15/0038; A61M 15/04; A61M 15/0041; A61M 15/00; A61M 15/0005; A61M 15/0006; A61M 15/0008; A61M 15/0013; A61M 15/0021; A61M 15/0086; A61M 15/0091; B26F 1/24; B26F 1/32; Y10T 83/0481
See application file for complete search history.

(56) References Cited

U.S. PATENT DOCUMENTS

| | | | |
|---|---|---|---|
| 4,889,114 A | 12/1989 | Kladders et al. | |
| 5,647,349 A * | 7/1997 | Ohki ................. | A61M 15/0028 128/203.12 |
| 5,685,294 A | 11/1997 | Gupte et al. | |
| 5,947,118 A | 9/1999 | Hochrainer et al. | |
| 2007/0017511 A1* | 1/2007 | Ohki ................. | A61M 15/0028 128/203.15 |
| 2007/0227217 A1* | 10/2007 | Halamoda ................. | B26F 1/24 72/71 |
| 2008/0160076 A1 | 7/2008 | Hochrainer et al. | |

(Continued)

*Primary Examiner* — Michael Tsai
(74) *Attorney, Agent, or Firm* — Lathrop Gage LLP

(57) ABSTRACT

A device for providing a medicament from capsules, where the device is integrated into an inhaler and comprises a capsule receiver comprising a capsule chamber, which extends along a first direction (X) in the manner of a tube and in which a capsule can be arranged, and a puncture device for opening the capsules, where the puncture device is arranged in a second direction (Y) radial to the capsule chamber, the puncture device having at least one needle which is moveable in sections into the capsule chamber in the second direction (Y) by means of an actuating button. A respective rear portion of the at least one needle of the puncture device is received in part in a needle receiver. The capsule receiver comprises at least one guide channel extending along the second direction (Y), wherein the needle receiver is arranged in the guide channel in such a moveable manner.

13 Claims, 7 Drawing Sheets

(56) References Cited

U.S. PATENT DOCUMENTS

| | | | |
|---|---|---|---|
| 2010/0175696 A1* | 7/2010 | Ishizeki | A61M 15/0028 128/203.15 |
| 2010/0288275 A1* | 11/2010 | Djupesland | A61M 15/0028 128/203.15 |
| 2011/0232637 A1* | 9/2011 | Kaemper | A61M 15/0028 128/203.12 |
| 2014/0076315 A1* | 3/2014 | Von Schuckmann | A61M 15/0028 128/203.15 |

* cited by examiner

DEVICE FOR OPENING CAPSULES

CROSS-REFERENCE TO RELATED APPLICATIONS

This patent application claims the benefit of priority from German application DE 10-2015-109-996.9, filed on Jun. 22, 2015, the contents of which are incorporated herein by reference.

BACKGROUND OF THE INVENTION

The invention relates to a device for opening capsules, which device is integrated into an inhaler and comprises a capsule receiver comprising a capsule chamber, which extends in a first direction (X) in the manner of a tube and in which a capsule (2) can be arranged, and a puncture device for opening the capsule, which puncture device is arranged in a second radial direction (Y) with respect to the capsule chamber, the puncture device having at least one needle which is moveable in part into the capsule chamber along the second direction (Y) by means of an actuating button.

Several principles by which inhalers operate are known in the prior art. The present invention relates to inhalers for the inhalation of medicaments in powder form from capsules. Such inhalers according to the invention are also called Bernoulli inhalers and are available on the market under the name HandiHaler, for example. The active ingredient in powder form is thereby stored in a capsule. These capsules are conventionally made of hard gelatine and consist of two cylindrical parts which are hemispherical at their ends. Such a capsule is disclosed in document DE 198 35 346 A1, for example.

Such a capsule is introduced into a generally cylindrical capsule chamber of the inhaler. This capsule chamber has an air inlet channel at one of its axial ends and an air outlet channel, which extends to the mouthpiece, at a further axial end. Furthermore, the dimensions of the capsule chamber are such that its length and width are greater than the dimensions of the capsule. However, the axial longitudinal axis of the capsule is nevertheless arranged substantially in parallel with an axial longitudinal axis of the capsule chamber.

Before inhalation, the capsule must first be opened. The inhaler has a puncture or cutting device for this purpose. This puncture device comprises two needles which are spaced apart along an axis in parallel with the axial longitudinal axis of the capsule chamber. The needles are pressed against the capsule by an actuating button, so that two openings are formed in the longitudinal lateral surface of the capsule. Some types of capsule have corresponding tapered portions of material at the puncture sites.

If air is then drawn in through the mouthpiece, an air stream is created in the capsule chamber from the air inlet to the air outlet channel. The air stream flowing past the openings generates a low pressure in front of the capsule openings compared with the interior of the capsule, so that the powder in the capsule is entrained in the air stream and thereby nebulised. In addition, the air stream causes the capsule to vibrate predominantly along the axial longitudinal axis. Owing to the dimensions of the capsule chamber already mentioned, the capsule is able to vibrate both vertically and horizontally.

Such inhalers are disclosed, for example, in documents DE 39 27 170 A1, DE 33 45 722 A1 and DE 43 18 455 A1.

Such inhalers of the generic type are disadvantageous in that the needles for opening the capsule are fixed directly to the actuating button. When the actuating button is moved, the needles scrape off plastics material at the openings in the capsule chamber owing to the tolerances. This creates plastics particles which lie in the region of the inhalation path. Furthermore, false air is drawn in through the needle openings in the capsule chamber. Some of the capsule inhalers available on the market additionally exhibit appreciable canting as well as in some cases an audible sound due to the unclear tolerance chains upon actuation of the actuating button.

Accordingly, the object of the present invention is to provide a device for opening capsules which is integrated into an inhaler, and respectively an inhaler having such a device, which avoid the disadvantages mentioned at the beginning.

SUMMARY OF THE INVENTION

The object is achieved by a device, integrated in an inhaler, for providing a medicament from capsules, which device comprises a capsule receiver comprising a capsule chamber, which extends in a first direction (X) in the manner of a tube and in which a capsule can be arranged, and a puncture device for opening the capsule, which puncture device is arranged in a second direction (Y) radial to the capsule chamber, the puncture device having at least one needle which is moveable in part into the capsule chamber along the second direction (Y) by means of an actuating button. This device is further characterised in that a respective rear portion of the at least one needle of the puncture device is received in part in a needle receiver, and in that the capsule receiver comprises, starting from the capsule chamber, at least one guide channel extending in the second direction (Y), wherein the needle receiver is arranged in the guide channel in such a manner that it is moveable.

The puncture device (5) preferably has two needles (6a, 6b) spaced apart along the first direction (X). Accordingly, preferably a rear portion of each of the two needles of the puncture device is received in part in a needle receiver. The capsule receiver comprises, starting from the capsule chamber, two guide channels extending along the second direction (Y). The needle receivers are movably arranged in the respective guide channel.

The needles of the puncture device for opening the capsules are fixedly connected to the needle receivers, the needle receivers being guided directly in a guide channel which is part of the same component, namely the capsule receiver, as the capsule chamber. Because the needle receivers are guided in guide channels, there are no or only very small gaps between the needle receiver and the guide channels. Consequently, little (at best no) air can be drawn through the guide channels into the capsule chamber. The amount of air drawn through the air inlet of the capsule chamber is thus increased. Undesirable effects, especially in the case of inhalers that operate by the Bernoulli principle (e.g. HandiHalers), are thereby reduced. Furthermore, the needles do not generate any wear on the guide channel or the capsule chamber respectively because on the one hand it is possible to equip the capsule chamber with large needle openings without too much false air being drawn into the capsule chamber, and on the other hand the use of the needle receivers also keeps the needles away from the boundaries of the guide channel or the capsule chamber respectively.

According to a preferred aspect of the invention, the at least one needle receiver is substantially in the form of a straight cylinder, preferably of a circular cylinder, and the at least one guide channel is in the form of a hollow cylinder having a preferably circular base. Alternatively, the straight cylinder and the corresponding hollow cylinder can also have alternative bases. In order to allow the at least one needle receiver to be moved in the guide channel, in this respect, the outer diameter of the needle receiver is smaller than the inner diameter of the guide channel. In this respect, a first end of the at least one guide channel preferably corresponds to a needle opening in the capsule chamber, wherein a second end of the at least one guide channel is open so that the needle receiver can be moved in sections beyond the guide channel.

An inner wall of the at least one guide channel preferably merges continuously into an inner wall of the capsule chamber. Advantageously, the at least one guide channel further has a narrowed portion at its first end. The size of the narrowed portion is preferably such that the needle is able to pass through the narrowed portion without touching the inner wall of the guide channel. Such a configuration allows the amount of false air drawn in to be reduced further.

According to a further preferred aspect of the invention, the at least one needle receiver can be moved by the actuating button against the force of a spring element arranged between the capsule receiver and the actuating button, starting from the maximum movement position along the second direction (Y) towards the capsule chamber and can be returned by the spring element to the maximum movement position again. The spring element preferably comprises a coil spring, the centre axis of which lies on a centre axis of the actuating button. However, alternative spring types, such as, for example, leg springs or torsion springs, are also conceivable. It is also conceivable to arrange several springs of this type between the capsule receiver and the actuating button. It would further be conceivable for the spring element to be realized in the form of an elastomer.

Consequently, preferably the at least one needle receiver is moveable along the second direction (Y) away from the capsule chamber only as far as a maximum movement position. The needle receiver preferably has a guide portion which is guided in the guide channel. Further preferably, the length of the guide portion is realized in such a manner that the guide portion remains in sections in the guide channel in the maximum movement position of the needle receiver. This configuration has the advantage that, even in the maximum movement position of the needle receivers, guiding thereof is ensured. Accordingly, the needle cannot cause any wear on the inner walls of the guide channels even in that position. Furthermore, it is ensured that no or only a small amount of false air is drawn in, since the guide portion rests at least in part in a sealing manner against the inner wall of the guide channel.

At least one further guide device is preferably arranged at the capsule receiver, in which guide device at least one guide projection of the actuating button is guided. Two guide projections are preferably arranged on the actuating button, which guide projections are guided in two guide devices. The two guide projections are preferably arranged at the outer ends of the actuating button along the second direction (Y). In particular, the guide projections of the actuating button are at the same distance from the spring element, or are respectively arranged symmetrically with respect to the centre axis of the actuating button. By means of such a configuration, tipping of the actuating button and thus canting of the guide projections in the guide devices is prevented upon operation. According to a particularly preferred embodiment, four guide projections are arranged on the actuating button, wherein two guide projections are in each case arranged so that the webs forming the guide channel can be received between them. By means of such a configuration, tipping of the actuating button upon actuation and thus canting of the guide projections in the guide devices is prevented. The actuating button is accordingly guided independently of the needles, so that clear tolerance chains are possible and lateral moments and canting of the actuating button are prevented. The sliding movement of the actuating button is accordingly improved.

According to a preferred embodiment, the actuating button has at least one receiver in which an end portion of the needle receivers is received. The actuating button preferably has two receivers, in each of which an end portion of the needle receivers is received. The receivers are arranged symmetrically with respect to a centre axis of the actuating button. Consequently, they are spaced apart symmetrically from the spring element. By means of such a configuration, canting of the needles in their guide channels is prevented upon actuation of the actuating button. The at least one receiver is realized preferably in the form of a cavity in the actuating button. In this respect, the actuating button has an opening leading to the at least one receiver. A clear length of the receiver extending along the second direction (Y) is preferably greater than a length of the end portion extending along the second direction (Y). As a result, the at least one needle receiver is loosely connected to the actuating button so that it can be guided in the device independently of the needle receiver. The tolerance chains on the button are limited considerably as a result, since the movement of the actuating button is only dependent on the setting of the button guide in a component of the device.

When the needle receiver is moved along the second direction (Y) towards the capsule chamber, an inner wall opposite the opening of the receiver is advantageously in contact with an end face of the end portion ($21a$, $21b$), so that a force can be transmitted from the actuating button to the needle receivers.

The at least one needle receiver preferably has an intermediate portion which is arranged between the guide portion and the end portion and extends through the opening of the actuating button leading to the at least one receiver. An outer diameter of the intermediate portion is preferably smaller than an outer diameter of the end portion. Further preferably, the inner diameter of the respective opening is greater than the outer diameter of the intermediate portion and smaller than the outer diameter of the end portion. When the needle receiver is moved along the second direction (Y) away from the capsule chamber, a transition edge of the end portion thus comes into contact with an inner wall ($34a$, $34b$) of the receiver ($20a$, $20b$) delimiting the opening ($24a$, $24b$), so that a force can be transmitted from the actuating button to the needle receiver.

When the actuating button is operated towards the capsule chamber, the actuating button is thus first moved until the inner wall of the receiver opposite the opening rests against the end face of the respective end portion of a needle receiver. By further movement of the actuating button, the contact between the inner wall and the end face causes force to be transmitted to the at least one needle receiver or respectively to the needle arranged on the needle receiver. After the capsule has been opened, the actuating button is released. By means of the spring force of the spring element, the actuating button is moved along the second direction away from the capsule chamber. Owing to the described larger dimensions of the clear length of the receiver, only the actuating button is moved at first until the transition edge of the end portion engages with an inner wall of the receiver delimiting the opening. When the actuating button is moved further by the spring element, the engagement causes the needle receiver to be carried along and moved to the maximum movement position.

According to a further aspect of the invention, the at least one needle receiver has a resilient lateral surface which rests in a sealing manner against an inner wall of the guide channels. The drawing in of false air is accordingly reduced further without impairing the ability of the needle receiver to slide in the guide channels.

According to a further embodiment, the two needles are of different lengths. By means of such a configuration it is possible first to open a first opening in the capsule according to a first movement path. The puncture device is accordingly moved only until the longer one of the two needles cuts a first opening in the capsule. Further movement of the puncture device towards the capsule then results in the shorter needle cutting an opening in the capsule. It is thus possible to open the two openings in the capsule in succession.

In a further aspect, the object of the invention is also achieved by an inhaler having a device for opening capsules according to one of the preceding embodiments.

Further advantages, objects and properties of the present invention will be explained by means of the following description of the accompanying figures. Equivalent components in the various embodiments can have the same reference numerals.

DETAILED DESCRIPTION OF THE INVENTION

Figure 1:
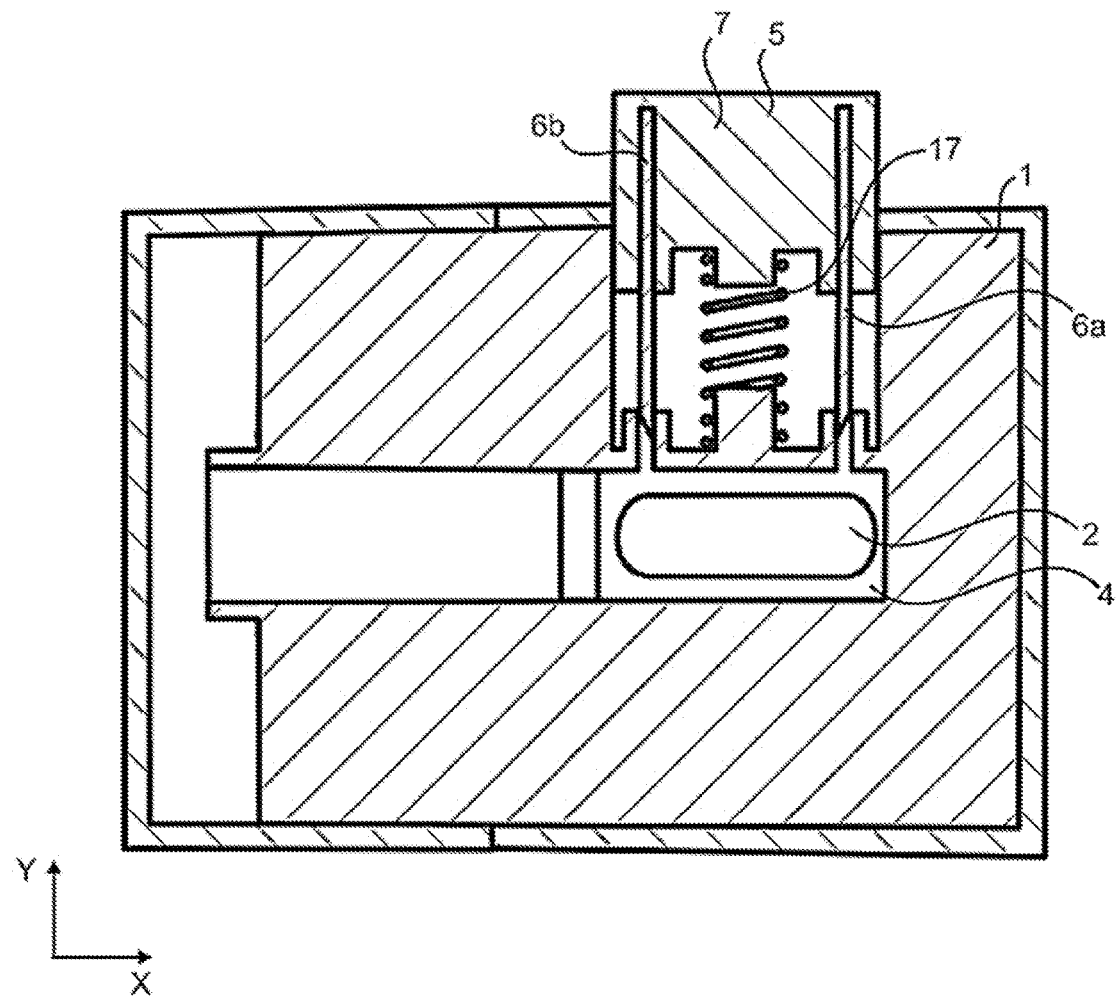
FIG. 1 shows a sectional view of a device for opening capsules according to the prior art integrated in an inhaler.

FIG. 1 shows a device (1) for opening capsules (2) according to the prior art integrated in an inhaler. The device (1) comprises a capsule chamber (4) in which a capsule (2) containing a medicament can be arranged. The capsule chamber (4) is of such a size that its length and width are greater than the dimensions of the capsule (2). However, an axial longitudinal axis of the capsule is nevertheless arranged substantially in parallel with an axial longitudinal axis of the capsule chamber (4). By means of an air stream in the capsule chamber from the air inlet channel (not shown) to the air outlet channel, the capsule (2) can vibrate predominantly along a first direction (X) but also along a second direction (Y). For opening the capsule (2), the device (1) has a puncture device (5). This puncture device (5) comprises two needles (6a, 6b) spaced apart along the first direction (X), and an actuating button (7). A spring element (17) is arranged between the puncture device (5) and the capsule chamber (4). By actuating the actuating button, the needles (6a, 6b) can be moved in sections into the capsule chamber (4) against the spring force of the spring element along the second direction (Y), so that the capsule (2) can be opened. The needles are fixed directly to the actuating button so that, when the actuating button (7) is moved, the needles (6a, 6b) scrape off plastics material at the needle openings (12a, 12b) in the capsule chamber (4) as a result of tolerances. Plastics particles which lie in the region of the inhalation path are thereby created. Furthermore, false air is drawn in through the needle openings (12a, 12b) in the capsule chamber (4).

Figure 2:
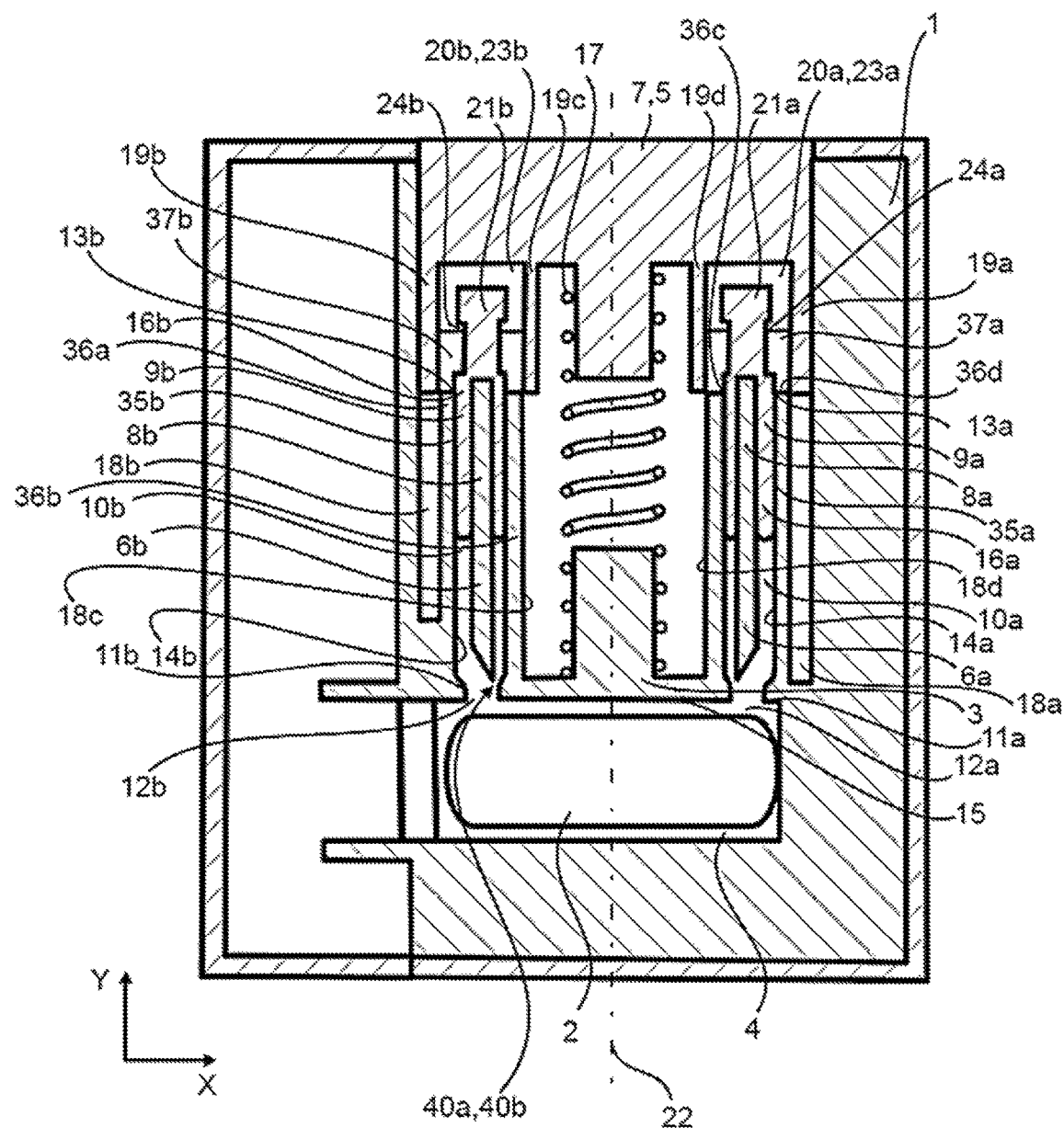
FIG. 2 shows a sectional view of a device for opening capsules integrated in an inhaler.

FIG. 2 shows a device (1) for opening capsules (2) integrated in an inhaler. The device (1) comprises a capsule receiver (3) having a capsule chamber (4) which extends along a first direction (X) in the manner of a tube and in which the capsule (2) is received. This capsule receiver (3) additionally comprises guide channels (10a, 10b) extending along the second direction (Y), starting from the capsule chamber (4).

The device (1) further contains a puncture device (5) for opening the capsule (2), which puncture device is arranged in a second direction (Y) radial to the capsule chamber (4). The puncture device (5) has two needles (6a, 6b) which are spaced apart along the first direction (X) and which can be moved in sections into the capsule chamber (4) along the second direction (Y) by means of an actuating button (7). In a forward portion (39a, 39b) oriented towards the capsule chamber (4), the needles (6a, 6b) have a cutting face (41a, 41b). The cutting face (41a, 41b) extends, starting from a tip (40a, 40b), obliquely outwards along the second direction (Y), that is to say away from a centre axis (22).

A rear portion (8a, 8b) of each of the needles (6a, 6b) is received in a needle receiver (9a, 9b). The needle receivers (9a, 9b) are in turn each arranged in a moveable manner in a guide channel (10a, 10b). The needle receivers (9a, 9b) can be cylindrical, for example, and the guide channels (10a, 10b) can accordingly be in the form of hollow cylinders. By using the needle receivers (9a, 9b), the needles (6a, 6b) are simultaneously kept away from the capsule chamber (4), that is to say the needles (6a, 6b) do not generate any wear on the capsule chamber (4).

In this respect, a first end (11a, 11b) of the guide channels (10a, 10b) corresponds to a needle opening (12a, 12b) in the capsule chamber (4), and a second end (13a, 13b) of the guide channels (10a, 10b) is open, so that the needle receiver (9a, 9b) is movable in sections beyond the guide channel (10a, 10b). The needle receivers (9a, 9b) are thus guided directly in a guide channel (10a, 10b) which is part of the same component, namely of the capsule receiver (3), as the capsule chamber (4). Accordingly, an inner wall (14a, 14b) of a guide channel (10a, 10b) merges continuously into an inner wall (15) of the capsule chamber (4), the guide channels (10a, 10b) having a narrowed portion at their first ends (11a, 11b). The narrowed portion is designed in such a way that the needles are able to pass through it without touching the inner walls (14a, 14b) of the guide channels (10a, 10b). It is thus ensured that a minimal amount of false air is drawn in through the needle openings (12a, 12b) in the capsule chamber (4). The needle receivers (9a, 9b) further have a guide portion (16a, 16b). This guide portion (16a, 16b) is guided in the guide channel (10a, 10b) and the length of the guide portion (16a, 16b) is such that, in the maximum movement position of the respective needle receiver (9a, 9b), the guide portion (16a, 16b) remains in sections in the guide channel (10a, 10b). Only a small or respectively no air gap remains between the lateral surface (35a, 35b) of the guide portion (16a, 16b) and the inner wall (14a, 14b). Advantageously, the lateral surface can also be formed by a resilient material. Accordingly, it is again ensured that only a minimal amount of false air is drawn in through the needle openings (12a, 12b) in the capsule chamber (4).

The needle receivers (9a, 9b) can be moved by the actuating button (7) against the force of a spring element (17), starting from the maximum movement position, along the second direction (Y) towards the capsule chamber (4) and can be returned to the maximum movement position again by the spring element (17). This spring element (17) is arranged in the form of a coil spring such that its centre axis lies on a centre axis (22) of the actuating button (7). The spring element (17) is arranged in an H-shaped receiver which is formed by the puncture device (5) and the capsule receiver (3). The maximum movement position of the needle receivers (9a, 9b) is thus given by the spring length of the spring element (17).

Four further guide devices (18a, 18b, 18c, 18d) are arranged on the capsule receiver (3), in which guide devices guide projections (19a, 19b, 19c, 19d) of the actuating button (7) are guided. These guide devices (19a, 19b, 19c, 19d) extend in parallel with respect to the guide channels (10a, 10b) for the needle receivers (9a, 9b) along the second direction (Y). The guide channels (10a, 10b) are thus delimited by webs (36a, 36b, 36c, 36d). The webs (36b, 36c) located on the inside relative to the centre axis (22) form in part the lateral boundary of the H-shaped receiver for the spring element (17). Two guide projections (18a, 18b, 18c, 18d) are respectively arranged on the puncture device (5) spaced apart in such a manner that the gap between the two forms one receiver (37a, 37b) for each guide channel (10a, 10b) respectively. An inner clear width, which extends along the first direction (X), between inner walls of two guide projections (18a, 18b, 18c, 18d) is thus greater than a width between the outer walls of the webs (35a, 35b, 35c, 35d) forming the guide channels. By means of such a configuration, an improvement in the sliding movement of the actuating button (7) for moving the needle receivers (9a, 9b) or the needles (6a, 6b) respectively is achieved. The actuating button (7) is guided independently of the needles (6a, 6b), so that clear tolerance chains are possible and lateral moments and canting of the actuating button (7) are thus prevented.

A clear length of the receivers (37a, 37b) for the guide channels (10a, 10b) extends along the second direction (Y) and is delimited by a wall portion (38a, 38b). In the case of maximum movement of the puncture device (5) towards the capsule chamber (3), the webs (35a, 35b, 35c, 35d) forming the guide channels abut the respective wall portion (38a, 38b). The maximum movement path of the puncture device (5) accordingly corresponds to the mentioned clear length of the receivers (37a, 37b) for the guide channels (10a, 10b).

Figure 3:
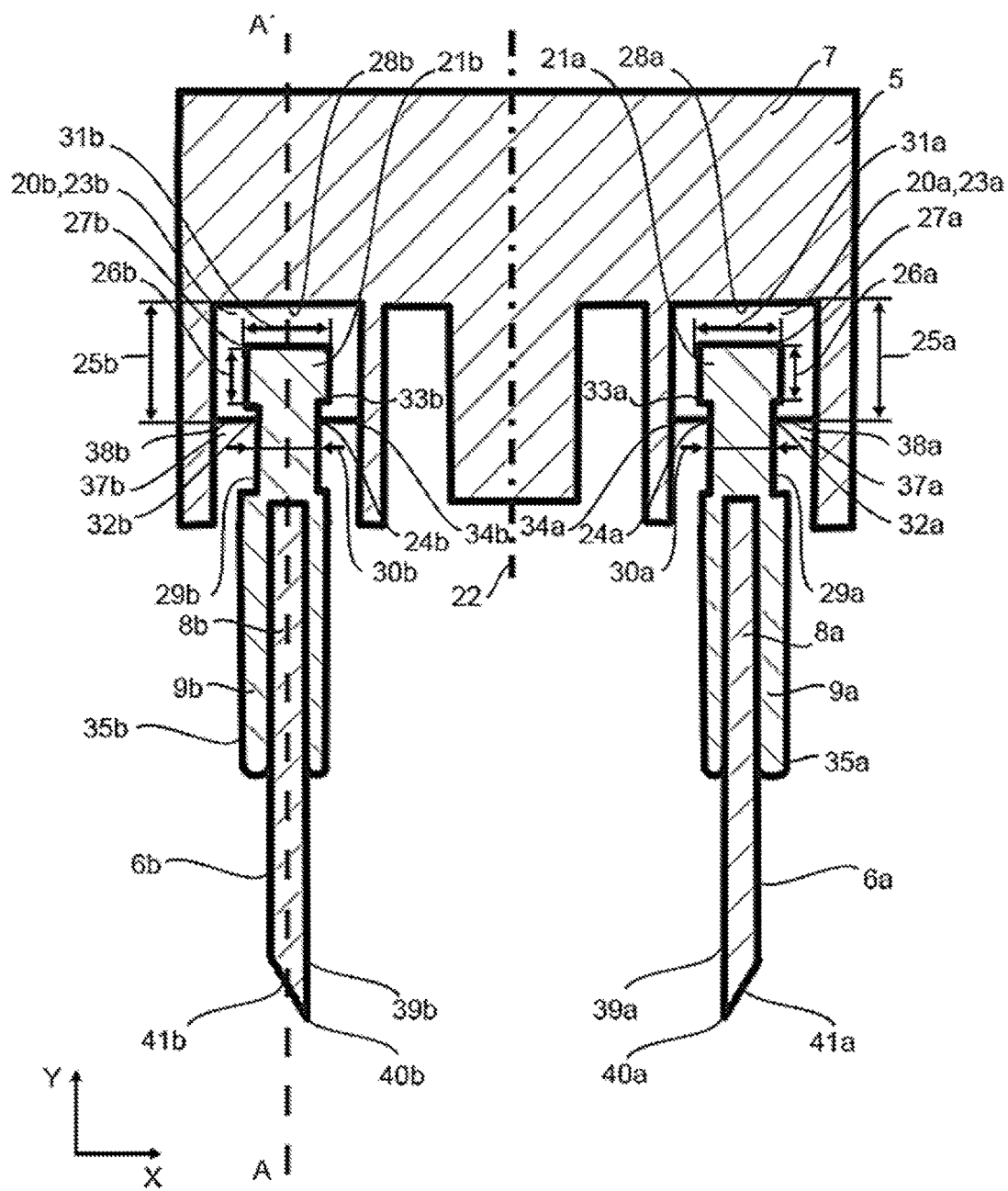
FIG. 3 shows a sectional view of the puncture device in detail.
Figure 4:
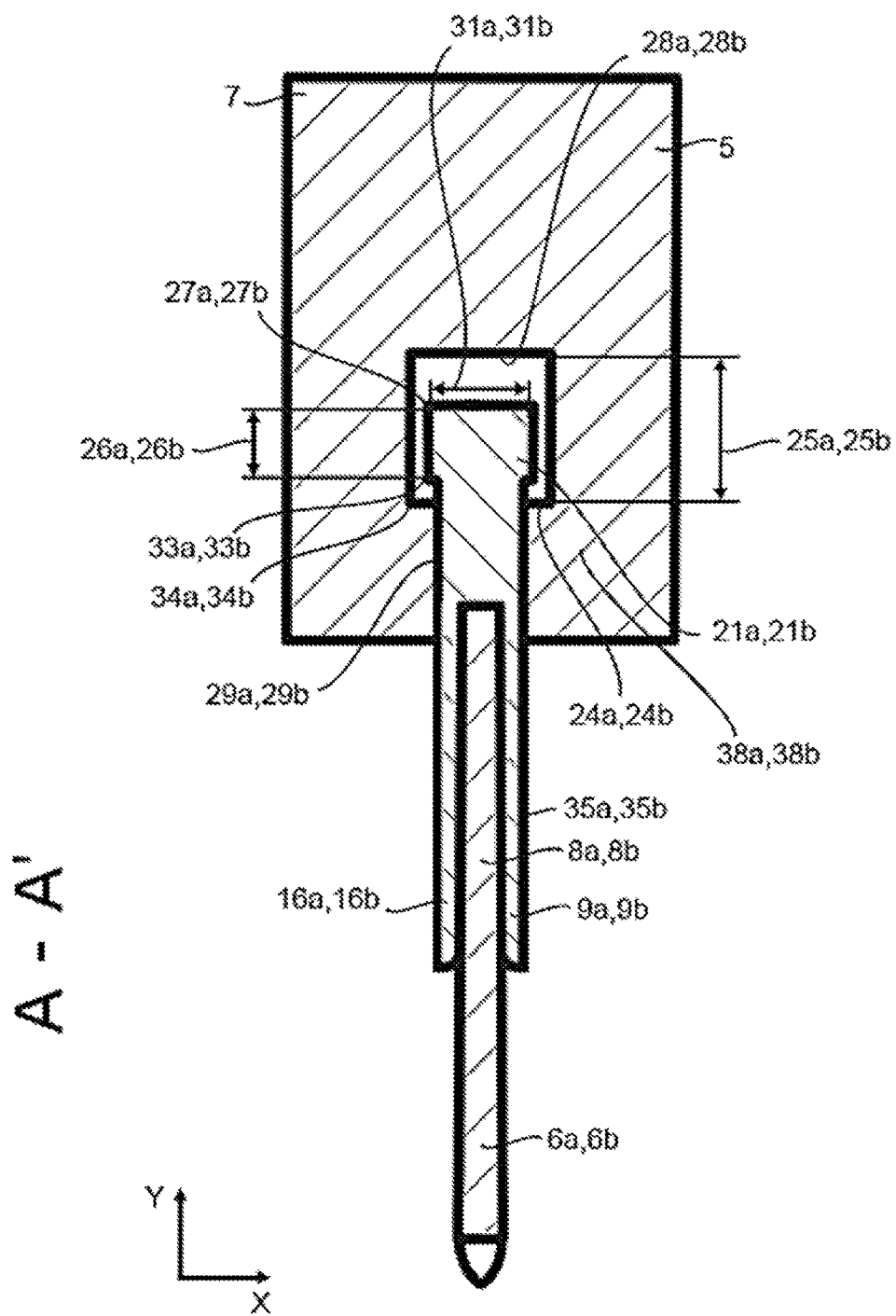
FIG. 4 shows a sectional view of a needle in the puncture device in detail.

The receivers (37a, 37b) for the guide channels (10a, 10b) are followed, when seen along the second direction (Y), by receivers (20a, 20b) for the needle receivers (9a, 9b) or an end portion (21a, 21b) of the needle receivers (9a, 9b) respectively. This can also be seen in FIGS. 3 and 4, in which the puncture device (5) is shown in detail, FIG. 4 being a sectional view along a cutting line A-A'. The wall portion (38a, 38b) in each case is a boundary between the receivers (20a, 20b) for the end portions (21a, 21b) and the receivers (37a, 37b) for the guide channels (10a, 10b). The receivers (20a, 20b) are further in the form of a cavity (23a, 23b) in the actuating button (7). The actuating button (7), or the respective wall portion (38a, 38b), has openings (24a, 24b) leading to the receivers (20a, 20b). A clear length (25a, 25b) of the receiver (20a, 20b) extending along the second direction (Y) is greater than a length (26a, 26b) of the end portion (21a, 21b) extending along the second direction (Y). Such a loose connection of the needle receivers (9a, 9b) to the actuating button (7) means that the actuating button can be guided in the device independently of the needle receivers (9a, 9b), so that the tolerance chains on the actuating button (7) are limited considerably and the movement of the actuating button (7) is dependent only on the setting of the button guide in a component of the device.

The receivers (20a, 20b) in each of which an end portion (21a, 21b) of the needle receivers (9a, 9b) is received, and the receivers (37a, 37b) for the guide channels are arranged symmetrically with respect to a centre axis (22) of the actuating button (7), so that a sliding movement of the actuating button (7) is ensured without canting.

The needle receivers (9a, 9b) further have an intermediate portion (29a, 29b) which is arranged between the guide portion (16a, 16b) and the end portion (21a, 21b) and extends through openings (24a, 24b) in the actuating button (7) that lead to the receivers (20a, 20b). An outer diameter (30a, 30b) of the intermediate portion (29a, 29b) is smaller than an outer diameter (31a, 31b) of the end portion (21a, 21b). Moreover, the inner diameter (32a, 32b) of the respective opening (24a, 24b) is larger than the outer diameter (30a, 30b) of the intermediate portion (29a, 29b) and smaller than the outer diameter (31a, 31b) of the end portion (21a, 21b). Accordingly, when the needle receiver (9a, 9b) is moved along the second direction (Y) away from the capsule chamber (4), a transition edge (33a, 33b) of the end portion (21a, 21b) is in contact with an inner wall (34a, 34b) of the receiver (20a, 20b) delimiting the opening (24a, 24b), so that a force can be transmitted from the actuating button (7) to the needle receivers (9a, 9b).

The end portions (21a, 21b) of the needle receivers (9a, 9b) further have an end face (27a, 27b). These end faces (27a, 27b) run in parallel with an inner wall (28a, 28b) opposite the opening in the receiver (20a, 20b). When the needle receiver (9a, 9b) is moved along the second direction (Y) towards the capsule chamber (4), a transmission of force from the actuating button (7) to the needle receivers (9a, 9b) or the needles (6a, 6b) respectively is possible as a result of each end face (27a, 27b) and each inner wall (28a, 28b), respectively, being in contact.

The actuation of the device (1) will be described in the following with reference to FIGS. 5 to 7.

Figure 5:
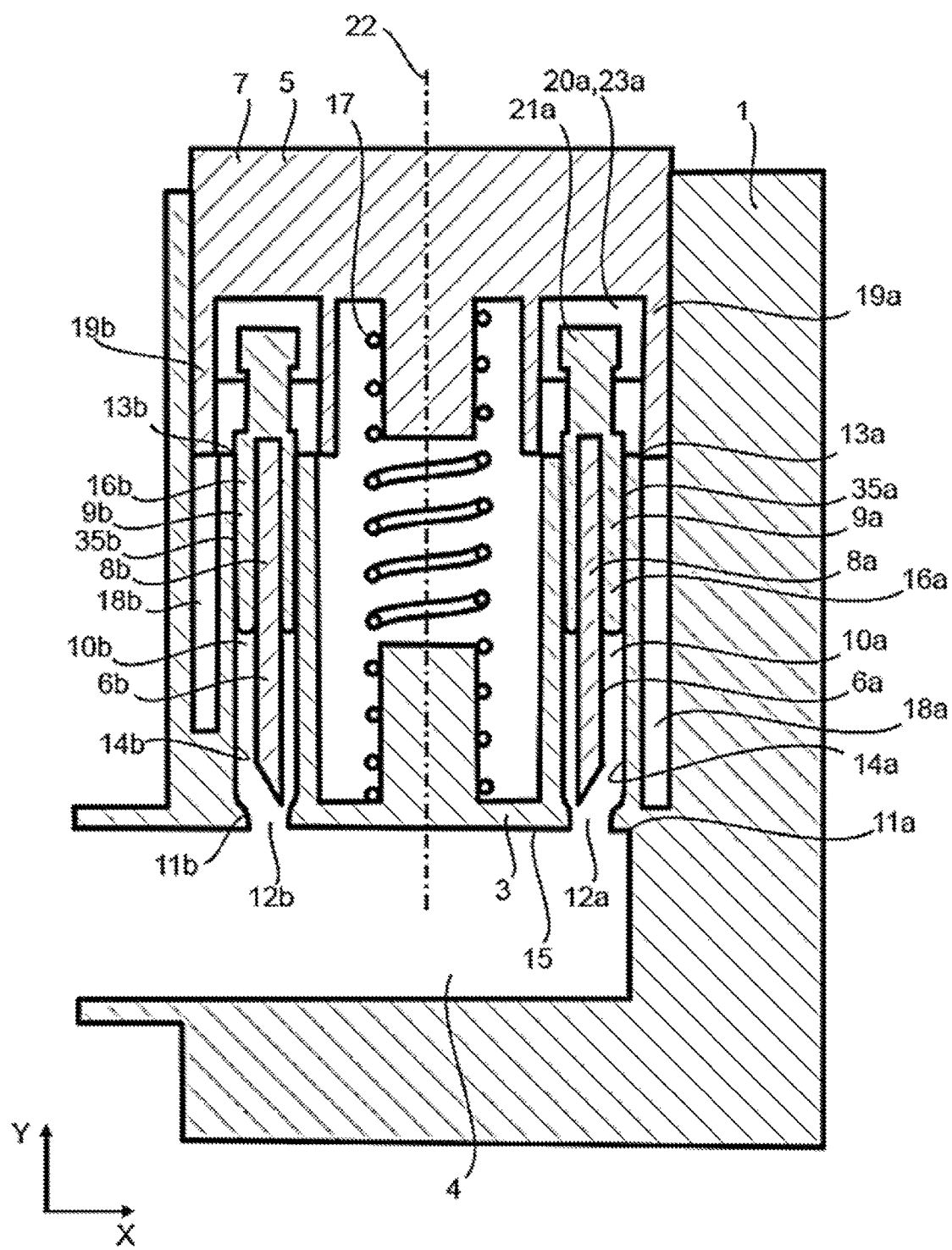
FIG. 5 shows a sectional view of a device for opening capsules integrated in an inhaler, in a starting position.

In FIG. 5, the puncture device is in a starting position. The spring element (17) determines the maximum movement position of the needle receivers (9a, 9b) or of the needles (6a, 6b) respectively by its spring length. In this position, the needles (6a, 6b) are positioned in the guide channels (10a, 10b). The guide portions (16a, 16b) of the needle receivers (9a, 9b) project only partially from the guide channels (10a, 10b). Accordingly, it is ensured even in this position that only a small amount of false air can be drawn in through the needle openings (12a, 12b) in the capsule chamber (4).

When the actuating button (7) is actuated towards the capsule chamber (3), the actuating button (7) is first moved until the inner wall (28a, 28b) of the receiver (20a, 20b) opposite the opening rests against the end face (27a, 27b) of each end portion (21a, 21b), respectively, of a needle receiver (9a, 9b). Further movement of the actuating button (7) causes force to be transmitted to the needle receivers (9a, 9b) or to the needles (6a, 6b) arranged in the needle receivers respectively as a result of the contact between the inner wall (28a, 28b) and the end face (27a, 27b).

Figure 6:
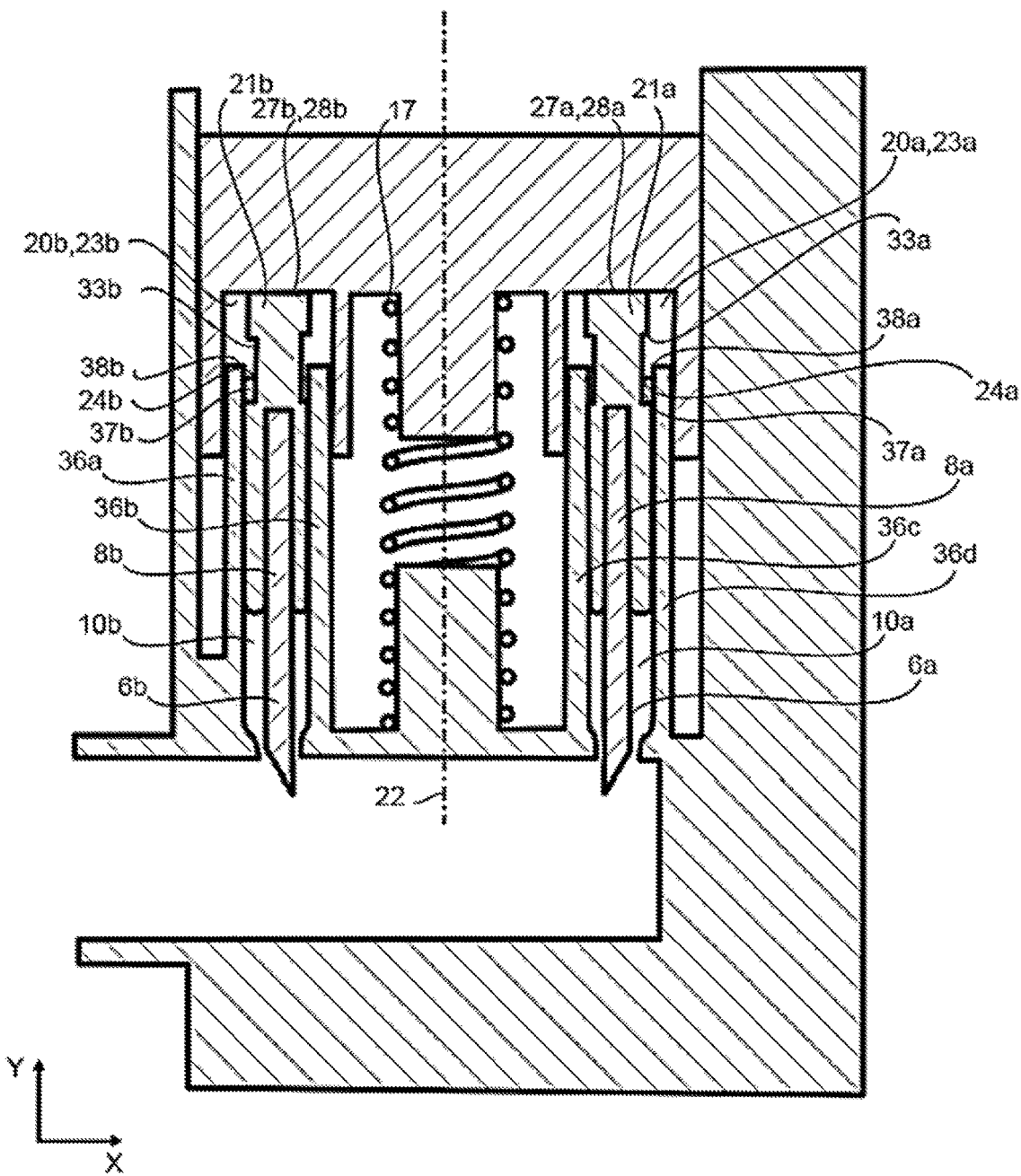
FIG. 6 shows a sectional view of a device for opening capsules integrated in an inhaler, in a maximum puncture position.
Figure 7:
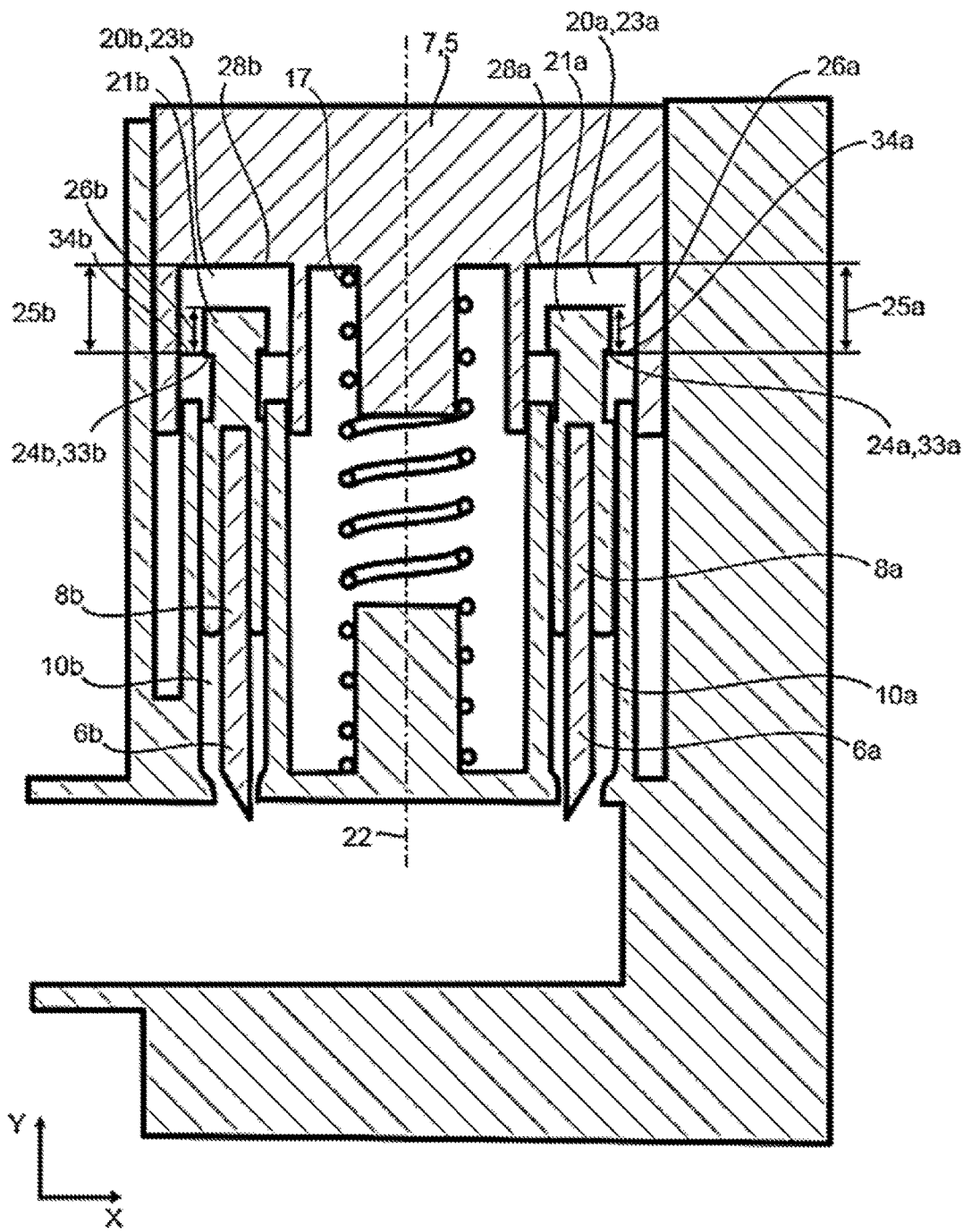
FIG. 7 shows a sectional view of a device for opening capsules integrated in an inhaler, in a retracted position.

FIG. 6 shows the device (1) in which the puncture device (5) has been moved to a maximum puncture position. The spring element (17) is thereby compressed. The needles (6a, 6b) project through the needle openings (12a, 12b) into the capsule chamber (4), whereby a capsule (not shown) would be opened. The webs (36a, 36b, 36c, 36d) forming the guide channels (10a, 10b) are received in the receivers (37a, 37b) and abut the respective wall portion (38a, 38b).

After the capsule (2) has been opened, the actuating button (7) is released. By means of the spring force of the spring element (17), the actuating button (7) is moved along the second direction (Y) away from the capsule chamber (4). Owing to the described larger dimensions of the clear length (25a, 25b) of the receiver (20a, 20b), only the actuating button (7) is moved at first, until the transition edge (33a, 33b) of the end portion (21a, 21b) engages with an inner wall (28a, 28b) of the receiver (20a, 20b) delimiting the opening. When the actuating button (7) is moved further by the spring element (17), the needle receivers (9a, 9b) are carried along as a result of the engagement. This is shown in FIG. 7. Finally, the puncture device (5) is moved to the maximum movement position according to FIG. 5.

All the features disclosed in the application documents are claimed as being essential to the invention, provided they are novel over the prior art individually or in combination.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Headings are used herein for convenience only.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. In the disclosure and the claims, "and/or" means additionally or alternatively. Moreover, any use of a term in the singular also encompasses plural forms.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

LIST OF REFERENCE NUMERALS 1 device for providing a medicament from capsules
2 capsule
3 capsule receiver
4 capsule chamber
5 puncture device
6a, 6b needles
7 actuating button
8a, 8b rear portion of the needles
9a, 9b needle receivers
10a, 10b guide channels
11a, 11b first end of the guide channels
12a, 12b needle openings
13a, 13b second end of the guide channels
14a, 14b the inner wall of a guide channel
15 an inner wall of the capsule chamber
16a, 16b guide portion
17 spring element
18a, 18b, further guide devices
18c, 18d further guide devices
19a, 19b, guide projections of the actuating button
19c, 19d guide projections of the actuating button
20a, 20b receivers
21a, 21b end portion of a needle receiver
22 centre axis of the actuating button
23a, 23b cavity
24a, 24b openings leading to the receivers
25a, 25b clear length of the receiver
26a, 26b length of the end portion extending along the second direction (Y)
27a, 27b end face of the end portion
28a, 28b inner wall opposite the opening of the receiver
29a, 29b intermediate portion
30a, 30b outer diameter of the intermediate portion
31a, 31b outer diameter of the end portion
32a, 32b inner diameter of the opening
33a, 33b transition edge of the end portion
34a, 34b inner wall of the receiver delimiting the opening
35a, 35b lateral surface of a needle receiver
36a, 36b webs forming the guide channel
36c, 36d webs forming the guide channel
37a, 37b receiver for the respective guide channel
38a, 38b wall portion
39a, 39b forward portion of the needles
40a, 40b tip of the needles
41a, 41b cutting face of the needles
X first direction
Y second direction

We claim:

1. A device for opening capsules, where said device is integrated into an inhaler and comprises a capsule receiver comprising a capsule chamber, which extends along a first direction (X) and in which a capsule is able to be arranged, and a puncture device for opening the capsule, where the puncture device is arranged in a second direction (Y) radial to the capsule chamber, wherein the puncture device has at least one needle, wherein at least a portion of the needle which is moveable into the capsule chamber along the second direction (Y) by means of an actuating button, wherein a rear portion of the at least one needle of the puncture device is received in part in at least one needle receiver and the capsule receiver comprises, starting from the capsule chamber, at least one guide channel extending along the second direction (Y), wherein the needle receiver is arranged in the guide channel so as to be moveable, wherein each of the at least one needle receiver comprises an end portion, an intermediate portion, and a guide portion, wherein the actuating button has at least one receiver in which the end portion of the at least one needle receiver is received, said intermediate portion is arranged between the guide portion and the end portion and extends through an opening in the actuating button leading to the at least one receiver, wherein an outer diameter of the intermediate portion is smaller than an outer diameter of the end portion, and the inner diameter of the opening is greater than the outer diameter of the intermediate portion and smaller than the outer diameter of the end portion, so that, when the needle receiver is moved along the second direction away from the capsule chamber, a transition edge of the end portion comes into contact with an inner wall delimiting the opening of the receiver, so that a force is able to be transmitted between the actuating button and the needle receiver.

2. The device according to claim 1, wherein the puncture device has two needles spaced apart along the first direction (X), wherein said at least one needle receiver comprises two needle receivers and said rear portion of each of the two needles is received in part in each of the two needle receivers, respectively.

3. The device according to claim 2, wherein the actuating button has two receivers in each of which said end portion of the needle receivers is received, wherein the two receivers are arranged symmetrically with respect to a centre axis of the actuating button.

4. The device according to claim 2, wherein the needles are of different lengths.

5. The device according to claim 1, wherein the needle receiver is substantially in the form of a straight circular cylinder and the at least one guide channel is in the form of a straight hollow cylinder having a circular base, wherein a first end of the at least one guide channel corresponds to a needle opening in the capsule chamber and wherein a second end of the at least one guide channel is open so that the needle receiver is able to be moved in sections beyond the guide channel.

6. The device according to claim 1, wherein an inner wall of the at least one guide channel merges continuously into an inner wall of the capsule chamber, wherein the at least one guide channel has a narrowed portion at its first end.

7. The device according to claim 1, wherein the needle receiver is able to be moved by the actuating button against the force of a spring element arranged between the capsule receiver and the actuating button, starting from a maximum movement position, along the second direction (Y) towards the capsule chamber and is able to be returned by the spring element to the maximum movement position again.

8. The device according to claim 1, wherein the needle receiver has a guide portion which is guided in the guide channel, wherein a portion of the guide portion always remains in the guide channel.

9. The device according to claim 1, wherein at least one guide device is arranged on the capsule receiver, wherein said at least one guide device comprises at least one guide projection for guiding the actuating button.

10. The device according to claim 1, wherein the at least one receiver is in the form of a cavity in the actuating button, wherein a clear length of the at least one receiver extending along the second direction is greater than a length of the end portion extending along the second direction.

11. The device according to claim 10, wherein, when the needle receiver is moved along the second direction towards the capsule chamber, an inner wall opposite the opening of the receiver comes into contact with an end face of the end portion, so that a force is able to be transmitted from the actuating button to the needle receiver.

12. The device according to claim 1, wherein the at least one needle receiver comprises a resilient lateral surface which rests in a sealing manner against an inner wall of the guide channels.

13. An inhaler comprising a device for providing a medicament from capsules according to claim 1.

* * * * *